LILAC PLANT

Filed June 18, 1973 2 Sheets-Sheet 1

United States Patent

Plant Pat. 3,695
Patented Mar. 25, 1975

3,695
LILAC PLANT

Leonard K. Slater, Agincourt, Ontaria, Canada, assignor of a fractional part interest to Sheridan Nurseries Ltd.

Filed June 18, 1973, Ser. No. 371,057
Int. Cl. A01h *5/00*
U.S. Cl. Plt.—66 1 Claim

This invention relates to a new and distinct variety of lilac plant, and particularly to a hybrid French Lilac *Syringa vulgaris.*

This new variety comes as a result of an extensive breeding program, and is a cross of another *Syringa vulgaris* hybrid developed by me and named "Agincourt Beauty" in the records of Sheridan Nurseries Ltd., of 700 Evans Avenue, Etobicoke, Ontario M9C 1A3, Canada, with an unnamed white seedling.

The present variety is distinguished from other French Lilac plants in that it has clear white flowers of the colour such as those found in the well known cultivar "Madame Lemoine," but the florets and flowers are much larger. The new variety exhibits tight spikes that are very well formed; and the plant grows to a height and width of about five feet, after which further growth appears to stop. Thus, the new variety of *Syringa vulgaris* according to the present invention is distinguished from other French Lilac hybrids by its compact growth habit and very large white florets and flowers, which are of the same colour as the variety "Madame Lemoine."

The new variety first flowered in 1964, and was evaluated in a population of about 150 seedlings of the cross "Agincourt Beauty" × unnamed white seedling, noted above, in 1965 when it was first years from seed. At that time, the seedling was about four feet in height, but had extremely large, white flowers. The spikes were tight, and well formed. The new variety was isolated, and grafts were first taken in 1965.

Since March 1965, grafts have been made on *Syringa vulgaris* seedlings in the inventor's garden; and this asexual reproduction has proven the characteristics of the new variety as being true.

Figure 1:
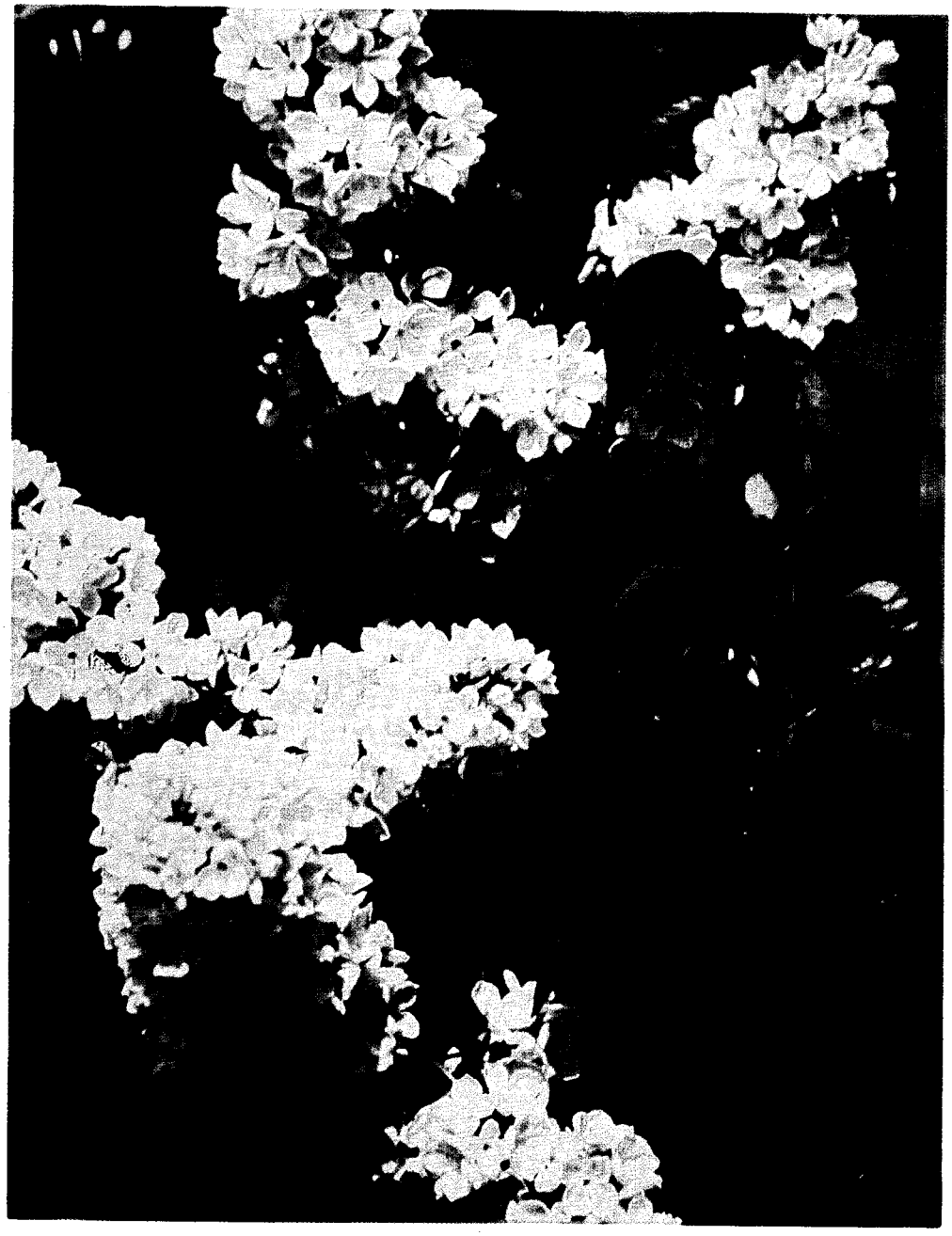
Figure 2:
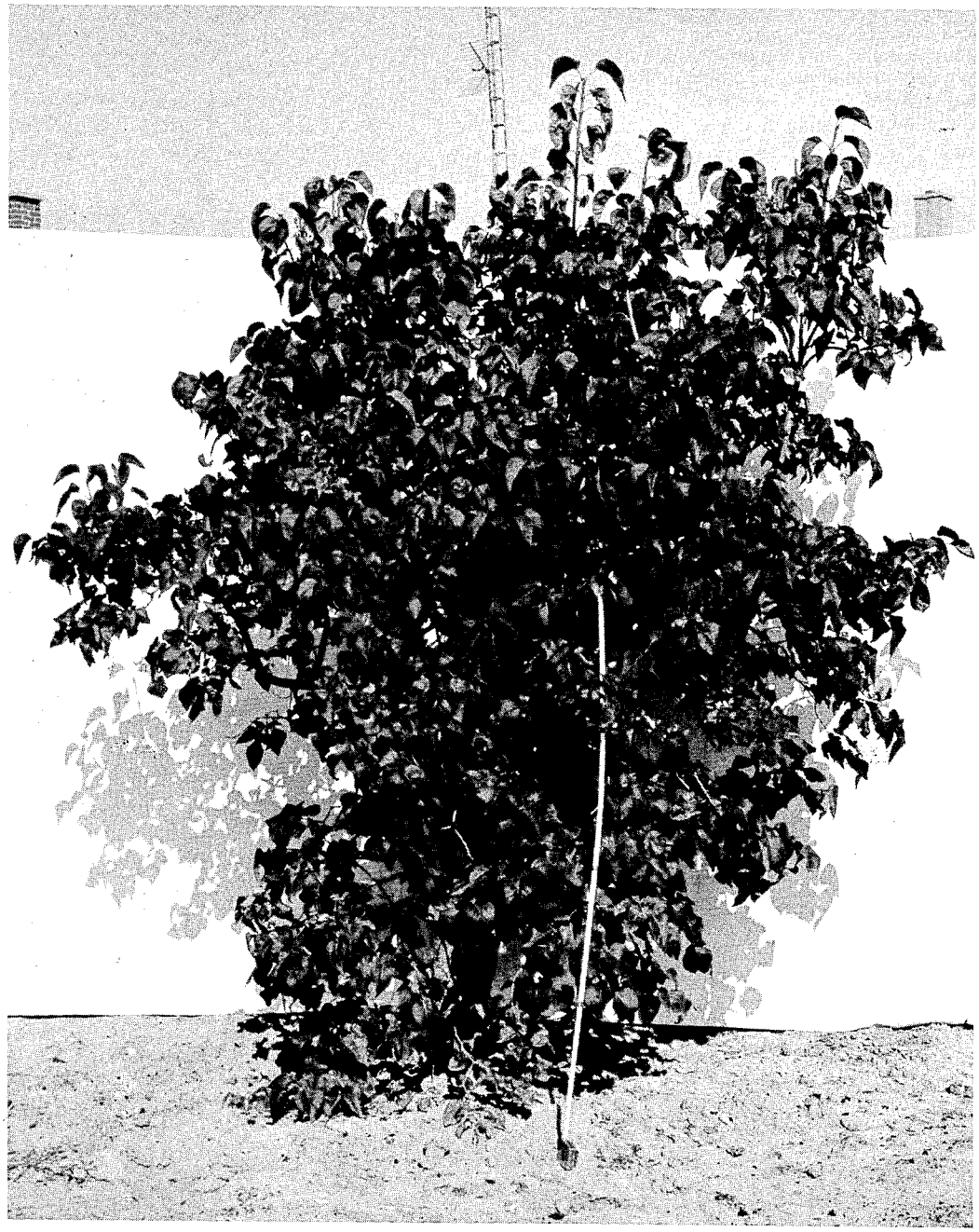

More detailed description of the present variety follows, taken together with the accompanying drawings, of which:

FIG. 1 is a colour photograph, showing as well as possible by this method of illustration, the shape and colour of the flower spikes of the matured plant according to this invention; and FIG. 2 is a black and white photograph illustrating the growth habit of the present variety.

THE PLANT

Type: French Lilac *Syringa vulgaris.*

Breeding: Hybrid.

Parentage: *Syringa vulgaris* "Agincourt Beatuty" × unnamed white seedling.

Growth habit: Compact growth habit, to about five to six feet high and about five feet wide in eight years; further growth in height apparently having ceased. The branches are stocky, coloured brown as is usual in French Lilac hybrid plants such as the variety "Madame Lemoine," with no lenticels.

Foliage: Numerous leaves, green, heart-shaped, about three inches long by one and one-half inches wide; medium thickness; smooth edges; medium petiole; and no glands.

Flower buds: Hardy; panicle-shaped; greenish yellow colour as is usual in such French Lilac hybrid plants as the variety "Madame Lemoine." The panicle is about 9 inches long, and its greatest width is about 6.5 inches. There are about 325 florets per panicle.

Flowers: Abundant flowers, first blooming about May 20 in the Toronto region, with full bloom about June 1st. The flowers are large, with tight spikes that are well formed. The colour is white, of substantially the same colour as the well known variety "Madame Lemoine," but larger. In each floret there are five petals, incurved, each about one inch across.

Fruit: Not abundant.

I claim:

1. A new and distinct variety of *Syringa vulgaris* hybrid French Lilac plant, characterized in that the mature plant is about five to six feet high and about five feet wide; and in that its flowers are white and very large when compared with other French Lilac hybrid plants, with large florets, and tight flowers spikes that are well formed.

No references cited.

ROBERT E. BAGWILL, Primary Examiner